(12) United States Patent
Freund et al.

(10) Patent No.: US 6,716,849 B1
(45) Date of Patent: Apr. 6, 2004

(54) SUBSTITUTED PHENYLCYCLOHEXANE CARBOXYLIC ACID AMIDES THAT HAVE AN ADENOSINE UPTAKE INHIBITING EFFECT

(75) Inventors: Wolf-Dietrich Freund, Leichlingen (DE); Stephan Lensky, Kürten (DE); Stephan Nicholas Müller, Wuppertal (DE); Holger Paulsen, Wuppertal (DE); Jörg Keldenich, Wuppertal (DE); Ervin Horváth, Leverkusen (DE); Joachim Schuhmacher, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/980,243

(22) PCT Filed: May 16, 2000

(86) PCT No.: PCT/EP00/04417
§ 371 (c)(1),
(2), (4) Date: Nov. 29, 2001

(87) PCT Pub. No.: WO00/73275
PCT Pub. Date: Dec. 7, 2000

(51) Int. Cl.[7] .................... A61K 31/496; C07D 403/04
(52) U.S. Cl. .................... 514/254.06; 544/370
(58) Field of Search ............... 544/370; 514/254.06

(56) References Cited

U.S. PATENT DOCUMENTS 5,229,505 A    7/1993  Bru-Magniez et al. ... 536/27.62
5,382,584 A    1/1995  Balasubramanian ........ 514/252
5,395,840 A    3/1995  Müller et al. ................ 514/300
5,607,962 A    3/1997  Müller-Gliemann et al. ..... 514/415
5,935,983 A    8/1999  Müller-Gliemann et al. ..... 514/397

FOREIGN PATENT DOCUMENTS

| CA | 2140709 | 7/1995 |
| EP | 0581003 | 2/1994 |
| EP | 0582164 | 2/1994 |
| EP | 0611767 | 8/1994 |
| EP | 0667342 | 8/1995 |
| EP | 0725061 | 8/1996 |
| EP | 0725064 | 8/1996 |

*Primary Examiner*—Joseph K. McKane
*Assistant Examiner*—Rebecca Anderson

(57) ABSTRACT

The present invention relates to substituted phenylcyclohexanecarboxamides of the formula (I) having adenosine-uptake-inhibiting action, to a process for their preparation and to their use in medicaments, in particular for treating ischaemic brain disorders.

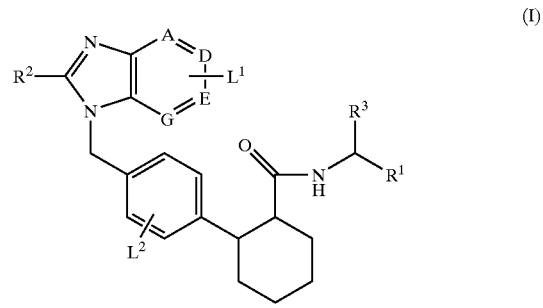

13 Claims, No Drawings

SUBSTITUTED PHENYLCYCLOHEXANE CARBOXYLIC ACID AMIDES THAT HAVE AN ADENOSINE UPTAKE INHIBITING EFFECT

The present invention relates to substituted phenylcyclohexanecarboxamides having adenosine-uptake-inhibiting action, to processes for their preparation and to their use in medicaments, in particular for treating ischaemic brain disorders.

Adenosine is an endogenic effector with cell-protective activity, in particular under cell-damaging conditions with limited oxygen and substrate supply, such as, for example, in ischaemia, stroke and brain trauma. The neuroprotective action of adenosine is essentially effected via suppression of presynaptic glutamate release and limitation of postsynaptic depolarization. This prevents toxic calcium influx into postsynaptic nerve cells via NMDA receptors. Under ischaemic or hypoxic conditions, the extracellular concentration of adenosine in the CNS is dramatically increased.

There are various indications of a neuroprotective, anticonvulsive, analgesic and sleep-inducing potential of adenosine-uptake inhibitors, since they enhance the intrinsic effects of adenosine by inhibiting its cellular reuptake. Accordingly, adenosine-uptake inhibitors can be administered orally or intravenously for the prevention and treatment of cerebral ischaemia, stroke, reperfusion damage, brain trauma, oedema, spasms, epilepsy, respiratory arrest, cardiac arrest, Reye's syndrome, cerebral thrombosis, emboli, tumours, haemorrhages, encephalomyelitis, hydroencephalitis, spinal injuries, post-operative brain damage, injuries to the retina or the optical nerve after glaucoma, ischaemia, hypoxia, oedema or trauma and in the treatment of schizophrenia, sleep disturbances and pain (*Cerebrovasc. Brain Metab. Rev.* 1992, 4, 364–369; *Drug Dev. Res.* 1993, 28, 410–415; *Science* 1997, 276, 1265–1268; 'Adenosine in the Nervous System', Ed.: Trevor Stone, Academic Press Ltd. 1991, 217–227; *Ann. Rep. Med. Chem.* 1998, 33. 111–120).

Adenosine-uptake inhibitors can also be employed for potentiating the effect of nucleobase, nucleoside or nucleotide antimetabolites in the chemotherapeutical treatment of cancer and antiviral (for example HIV) chemotherapy (*Curr. Med. Chem.* 1997, 4, 35–66).

EP-A0 611 767 and EP-A-0 725 064 disclose phenylcyclohexylcarboxamides which can be used for treating atherosclerosis and/or restenosis.

The present invention relates to compounds of the general formula (I)

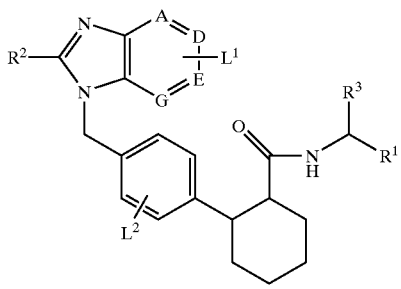

(I), in wherein

A, D, E and G are identical or different and represent CH groups or nitrogen atoms, $L^1$ and $L^2$ are identical or different and independently of one another each represents one or more radicals selected from the group consisting of hydrogen, halogen, hydroxyl, carboxyl, cyano, nitro, trifluoromethyl, trifluoromethoxy, $(C_1-C_6)$-alkyl, $(C_1-C_6)$-alkoxy or $(C_1-C_6)$-alkoxy-carbonyl, $R^1$ represents the $CH_2$—OH group, or
represents a radical of the formula CO—$NR^4R^5$
in which
$R^4$ and $R^5$ are identical or different and each represents hydrogen or $(C_1-C_6)$-alkyl, $R^2$ represents $(C_3-C_8)$-cycloalkyl,
represents $(C_1-C_8)$-alkyl which is optionally interrupted by an oxygen or sulphur atom or by a radial $NR^6$.
represents a 4 to 8-membered saturated heterocycle which is attached to the imidazole ring via a nitrogen atom and which optionally contains a further oxygen or sulphur atom, or
represents a 4- to 8-membered saturated heterocycle which contains a radical of the formula $NR^7$ and optionally additionally one nitrogen, oxygen or sulphur atom,
where $(C_3-C_8)$cycloalkyl, $(C_1-C_8)$-alkyl which is optionally interrupted by one oxygen or sulphur atom, the 4- to 8-membered saturated heterocycle which is attached to the imidazole ring via a nitrogen atom and which optionally contains one further oxygen or sulphur atom and optionally $(C_1-C_8)$-alkyl which is interrupted by a radical $NR^6$ and optionally the 4 to 8-membered saturated heterocycle which contains a radical of the formula $NR^7$ and optionally additionally one nitrogen, oxygen or sulphur atom are substituted by one to three hydroxyl groups and/or by a radical of the formula —$NR^8R^9$
in which
$R^6$ and $R^7$ are identical or different and each represents hydrogen, $(C_1-C_6)$-alkyl, hydroxy-$(C_1-C_6)$-alkyl or $(C_3-C_7)$-cycloalkyl.
$R^8$ and $R^9$ are identical or different and each represents hydrogen, $(C_1-C_6)$-alkyl or $(C_3-C_7)$-cycloalkyl, or
$R^8$ and $R^9$ together with the nitrogen atom form a 4- to 8-membered saturated heterocycle which may optionally additionally contain one oxygen or sulphur atom or a radical of the formula $NR^{10}$
in which
$R^{10}$ represents hydrogen, $(C_1-C_6)$alkyl or $(C_3-C_7)$-cycloalkyl and $R^3$ represents a phenyl, naphthyl, pyrimidinyl, pyridyl, furyl or thienyl ring, where the rings are optionally mono- or polysubstituted by radicals selected from the group consisting of halogen, hydroxyl, carboxyl, cyano, nitro, trifluoromethyl, trifluoromethoxy, $(C_1-C_6)$-alkyl, $(C_1-C_6)$-alkoxy or $(C_1-C_6)$-alkoxycarbonyl, and their salts.

Physiologically acceptable salts of the compounds according to the invention can be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

The compounds of the general formula (I) according to the invention can occur in different stereoisomeric forms which are either like image and mirror image (enantiomers), or which are not like image and mirror image (diastereomers). The invention relates both to the enantiomers and to the diastereomers and their respective mixtures. The racemic forms, like the diastereomers, can be separated in a known manner into the stereoisomerically uniform components.

Furthermore, certain compounds can be present in tautomeric forms. This is known to the person skilled in the art, and such compounds are likewise included in the scope of the invention.

$(C_1-C_8)$-Alkyl, $C_1-C_6$-alkyl etc., represent a straight-chain or branched alkyl radical having 1 to 8 or 1 to 6 carbon atoms. Examples which may be mentioned are: methyl, ethyl, n-propyl, isopropyl, tert-butyl, n-pentyl and n-hexyl. Preference is given to a straight-chain or branched alkyl radical having 1 to 4 carbon atoms $(C_1-C_4)$. Particular preference is given to a straight-chain or branched alkyl radical having 1 to 3 carbon atoms $(C_1-C_3)$.

$(C_1-C_8)$-Alkyl, $(C_1-C_6)$-alkyl etc., which is interrupted by one oxygen or sulphur atom and which is substituted by one to three hydroxyl groups and/or by a radical of the formula $-NR^8R^9$ represents, for example, 1,3-dihydroxy-prop-2-oxy-methyl, 2-hydroxy-ethoxy-methyl, 2-hydroxy-prop-1-oxy-methyl, 3-hydroxy-prop-1-oxy-methyl, morpholin-4-yl-methyl, piperidin-1-yl-methyl, 2-amino-ethyl, 2-dimethylamino-ethyl or diethylamino-methyl.

$(C_1-C_8)$-Alkyl, $(C_1-C_6)$-alkyl etc., which is interrupted by a radical $N^6$ and which is optionally substituted by one to three hydroxyl groups and/or by a radical of the formula $-NR^8R^9$ represents, for example, N-(2-hydroxy-ethyl)-aminomethyl, N-(2-hydroxy-ethyl)-N-methyl-aminomethyl or N,N-bis-(2-hydroxy-ethyl)-aminomethyl.

Hydroxy-$(C_1-C_6)$-alkyl or hydroxy-$(C_1-C_4)$-alkyl represents a straight-chain or branched alkyl radical having 1 to 6 or 1 to 4 carbon atoms. The examples which may be mentioned are: hydroxymethyl, 2-hydroxy-ethyl, 2-hydroxy-prop-1-yl, 3-hydroxy-prop-1-yl, 3-hydroxy-prop-2-yl, 2-hydroxy-but-1-yl, 5-hydroxy-pent-1-yl and 6-hydroxy-hex-1-yl. Preference is given to 2-hydroxy-ethyl.

$(C_1-C_6)$-Alkoxy represents a straight-chain or branched alkoxy radical having 1 to 6 carbon atoms. Examples which may be mentioned are: methoxy, ethoxy, n-propoxy, isopropoxy, tert-butoxy, n-pentoxy and n-hexoxy. Preference is given to a straight-chain or branched alkoxy radical having 1 to 4 carbon atoms $(C_1-C_4)$. Particular preference is given to a straight-chain or branched alkoxy radical having 1 to 3 carbon atoms $(C_1-C_3)$.

$(C_1-C_6)$-Alkoxycarbonyl represents a straight-chain or branched alkoxycarbonyl radical having 1 to 6 carbon atoms. Examples which may be mentioned are: methoxycarbonyl, ethoxycarbonyl, n-propoxycarbonyl, isopropoxycarbonyl and tert-butoxycarbonyl. Preference is given to a straight-chain or branched alkoxycarbonyl radical having 1 to 4 carbon atoms $(C_1-C_4)$. Particular preference is given to a straight-chain or branched alkoxycarbonyl radical having 1 to 3 carbon atoms $(C_1-C_3)$.

$(C_3-C_8)$-Cycloalkyl, $(C_3-C_7)$-cycloalkyl etc., represents, in the context of the invention, cyclopropyl, cyclobutyl, cyclopentyl, cyclohexyl, cycloheptyl or cyclooctyl. Cyclopropyl, cyclopentyl and cyclohexyl may be mentioned as being preferred.

Halogen in the context of the invention generally represents fluorine, chlorine, bromine and iodine. Preference is given to fluorine, chlorine and bromine. Particular preference is given to fluorine and chlorine.

In the context of the invention, a 4- to 8-membered (preferably 5- to 7-membered) saturated heterocycle which is attached via a nitrogen atom and which optionally contains one further oxygen or sulphur atom represents, for example, pyrrolidin-1-yl, piperidin-1-yl, morpholin-4-yl, thiomorpholin-4-yl or 1H-hexahydroazepin-1-yl.

In the context of the invention, a 4- to 8-membered (preferably 5- to 7-membered) saturated heterocycle which contains a radical of the formula $NR^7$ and optionally additionally one nitrogen, oxygen or sulphur atom represents, for example, pyrrolidin-2-yl, 1-methylpyrrolidin-2-yl, pyrrolidin-3-yl, pyrazolidin-1-yl, piperidin-2-yl, 1-isopropyl-piperidin-3-yl, morpholin-2-yl, 4-cyclohexyl-piperazin-1-yl, thiomorpholin-3-yl, 1-ethyl-1H-hexahydroazepin-3-yl or 4-methyl-1H-hexahydro-1,4-diazepin-1-yl. This heterocycle can be attached to the imidazole ring via a ring carbon atom or a ring nitrogen atom.

Preference is given to compounds of the general formula (I) which have the absolute configuration given in the general formula (I')

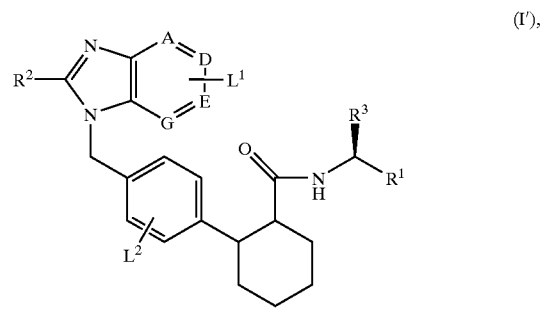

(I'),

The compounds according to the invention can be present in four different relative configurations (A) to (D):

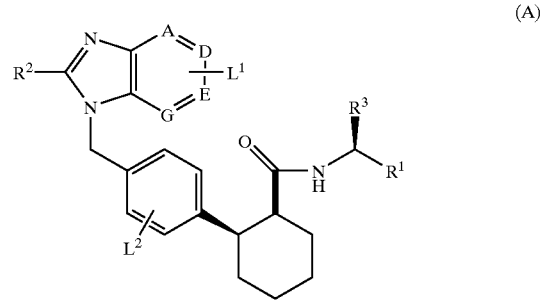

(A)

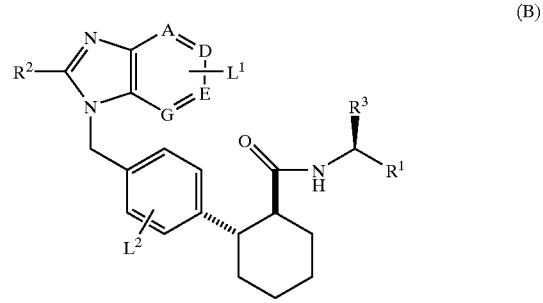

(B)

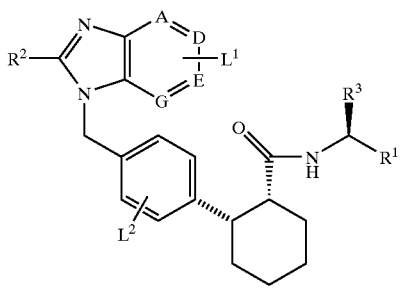

(C)

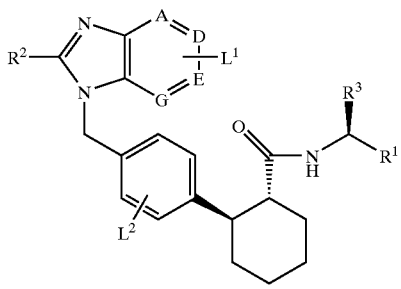

(D)

Preference is given to the configuration (D).

Preference is likewise given to compounds of the general formula (I) in which $R^1$ represents a radical of the formula CO—$R^4R^5$ where $R^4$ and $R^5$ are each as defined above. Moreover, preference is given to those compounds of the general formula (I) in which $R^2$ contains a basic nitrogen atom.

Basic nitrogen atom is to be understood as meaning a nitrogen atom which, after protonation of the compound under aqueous standard conditions, has a pKa of more than 6.

Particular preference is given to compounds of the general formula (I) according to the invention
where
A, D, E and G each represent the CH group,
or one of the radicals A, D, E and G represents a nitrogen atom and the others each represent the CH group, $L^1$ and $L^2$ are identical or different and independently of one another each represents one or more radicals selected from the group consisting of hydrogen, fluorine, chlorine, cyano, trifluoromethyl or trifluoromethoxy, $R^1$ represents the —$CH_2$—OH group, or
represents a radical of the formula —CO—$NR^4R^5$
in which
$R^4$ and $R^5$ are identical or different and each represents hydrogen or ($C_1$–$C_3$)-alkyl.

$R^2$ represents ($C_3$–$C_7$)-cycloalkyl,
represents ($C_1$–$C_6$)-alkyl which is optionally interrupted by an oxygen or sulphur atom or by a radical $NR^6$,
represents a 5- to 7-membered saturated heterocycle which is attached to the imidazole ring via a nitrogen atom and which optionally contains a further oxygen or sulphur atom, or
represents a 5- to 7-membered saturated heterocycle which contains a radical of the formula $NR^7$ and optionally additionally one nitrogen, oxygen or sulphur atom,
where ($C_3$–$C_7$)-cycloalkyl, ($C_1$–$C_6$)-alkyl which is optionally interrupted by one oxygen or sulphur atom, the 5- to 7-membered saturated heterocycle which is attached to the imidazole ring via a nitrogen atom and which optionally contains one further oxygen or sulphur atom and optionally ($C_1$–$C_6$)-alkyl which is interrupted by a radical $NR^6$ and optionally the 5- to 7-membered saturated heterocycle which contains a radical of the formula $NR^7$ and optionally additionally one nitrogen, oxygen or sulphur atom are substituted by a hydroxyl group and/or by a radical of the formula —$NR^8R^9$
in which
$R^6$ and $R^7$ are identical or different and each represents hydrogen, ($C_1$–$C_4$)-alkyl hydroxy-($C_1$–$C_4$)-alkyl or ($C_3$–$C_6$)-cycloalkyl.

$R^8$ and $R^9$ are identical or different and each represents hydrogen, ($C_1C_4$)-alkyl or ($C_3$–$C_6$)-cycloalkyl,
or
$R^8$ and $R^9$ together with the nitrogen atom form a 5- to 7-membered saturated heterocycle which may optionally additionally contain one oxygen or sulphur atom or a radical of the formula $NR^{10}$
in which
$R^{10}$ represents hydrogen, ($C_1$–$C_4$)-alkyl or ($C_3$–$C_6$)-cycloalkyl
and
$R^3$ represents a phenyl, pyridyl or thienyl ring which is optionally mono- or polysubstituted by radicals selected from the group consisting of fluorine, chlorine, cyano, trifluoromethyl or trifluoromethoxy,
and their salts.

Very particular preference is given to compounds of the general formula (I)
where
A, D and E each represent a CH group,
G represents a nitrogen atom or represents a CH group,
$L^1$ and $L^2$ each represent hydrogen.
$R^1$ represents a radical of the formula —CO—$NR^4R^5$,
in which
$R^4$ and $R^5$ each represent hydrogen,
$R^2$ represents ($C_1$–$C_4$)-alkyl which is optionally interrupted by one oxygen atom, or
represents a 4-$R^7$-piperazin-1-yl radical
where ($C_1$–$C_4$)-alkyl which is optionally interrupted by one oxygen atom is substituted by a hydroxyl group or by a radical of the formula —$NR^8R^9$
in which
$R^7$ represents hydrogen, ($C_1$–$C_4$)-alkyl or ($C_3$–$C_6$)-cycloalkyl,
$R^8$ and $R^9$ arm identical or different and each represents hydrogen, ($C_1$–$C_4$)-alkyl or ($C_3$–$C_6$)-cycloalkyl,
or
$R^8$ and $R^9$ together with the nitrogen atom form a morpholine radical,
and
$R^3$ represents a phenyl radical,
and their salts.

Moreover, processes for preparing the compounds of the general formula (I) have been found which are characterized in that

[A] compounds of the general formula (II)

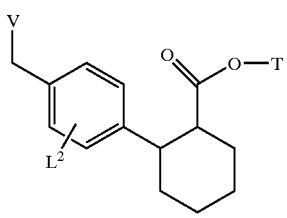

in which

L² is as defined above,

T represents $(C_1-C_4)$-alkyl, preferably methyl or tert-butyl, and

V represents a suitable leaving group, such as, for example, halogen, mesylate or tosylate, preferably bromine, is initially converted by reaction with compounds of the general formula (III)

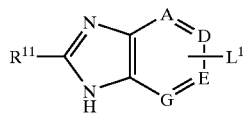

in which

A, D, E, G and L¹ are each as defined in claim 1 and $R^{11}$ has the meaning of $R^2$ given in claim 1, where amino and hydroxyl functions are optionally blocked by suitable amino or hydroxyl protective groups, in inert solvents, depending on the definition of $R^{11}$ optionally in the presence of a base, into the compounds of the general formula (IV)

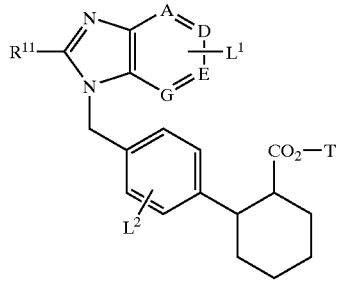

in which $R^{11}$, A, D, E, G, $L^1$, $L^2$ and T are each as defined above, which are converted in a subsequent step using acids or bases into the corresponding carboxylic acids of the general formula (V)

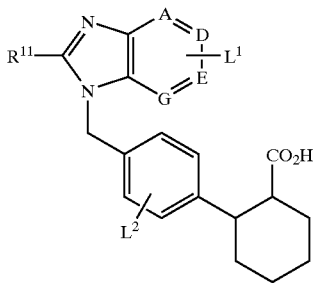

in which $R^{11}$, A, D, E, G, $L^1$ and $L^2$ are each as defined above, which are subsequently, following activation, reacted by known methods with compounds of the general formula (VI)

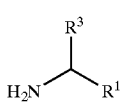

in which $R^1$ and $R^3$ are each as defined above in inert solvents, and, if $R^{11}$ carries one of the abovementioned protective groups, these are optionally removed by customary methods either in the hydrolysis to the acids (IV)→(V) or after the reaction with the compounds of the general formula (VI), or

[B] if $R^2$ represents a saturated heterocycle which is attached directly via a nitrogen atom to the imidazole ring, the abovementioned compounds of the general formula (II) are initially converted with compounds of the general formula (IIIa)

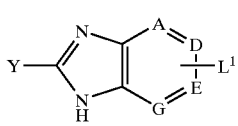

in which

A, D, E, G and L¹ are each as defined above

Y represents halogen or mesyl, preferably chlorine, bromine or mesyl, in inert solvents into the corresponding compounds of the formula (VII)

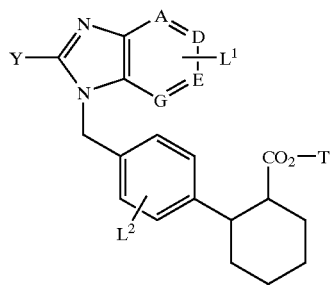

(VII), in which
Y, A, D, E, G, $L^1$, $L^2$ and T are each as defined above,
which are reacted in a subsequent step with compounds
of the general formula (VIII)

$HNR^{12}R^{13}$ (VIII)

in which
$R^{12}$ and $R^{13}$ together with the nitrogen atom form a
heterocycle according to the definition of $R^2$
to give compounds of the general formula (IX)

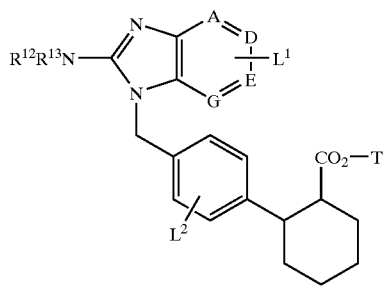

(IX), in which
A, D, E, G, $L^1$, $L^2$, $R^{12}$, $R^{13}$ and T are each as defined above,
which are, in the subsequent steps, converted as described under [A] by hydrolysis into the corresponding carboxylic acids of the general formula (X)

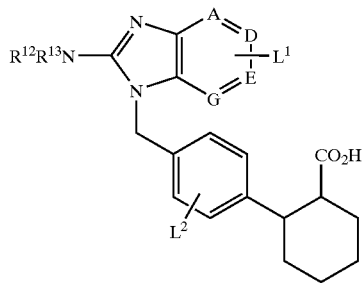

(X), in which
A, D, E, G, $L^1$, $L^2$, $R^{12}$ and $R^{13}$ are each as defined above,
and these compounds are subsequently, following activation, reacted with the compounds of the general formula (VI) according to known methods for preparing amides from carboxylic acids and amines and, if appropriate, converted into the corresponding salts by reaction with an acid.

The processes according to the invention can be illustrated in an exemplary manner by the formula schemes below:

[A]

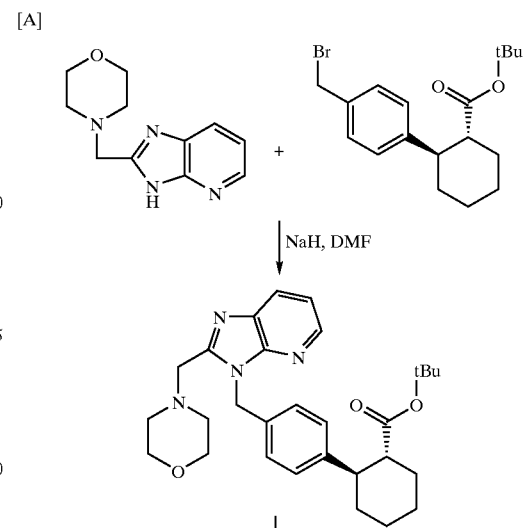

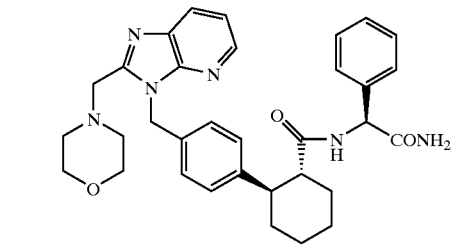

[B]

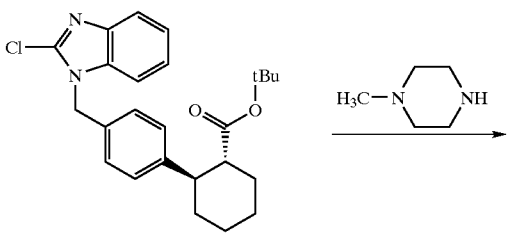
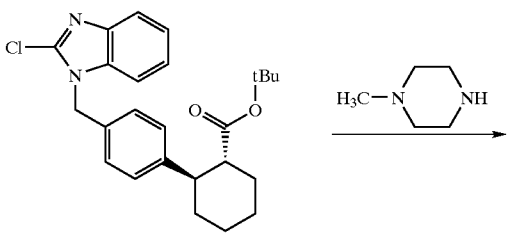
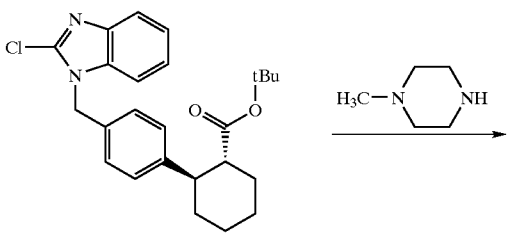

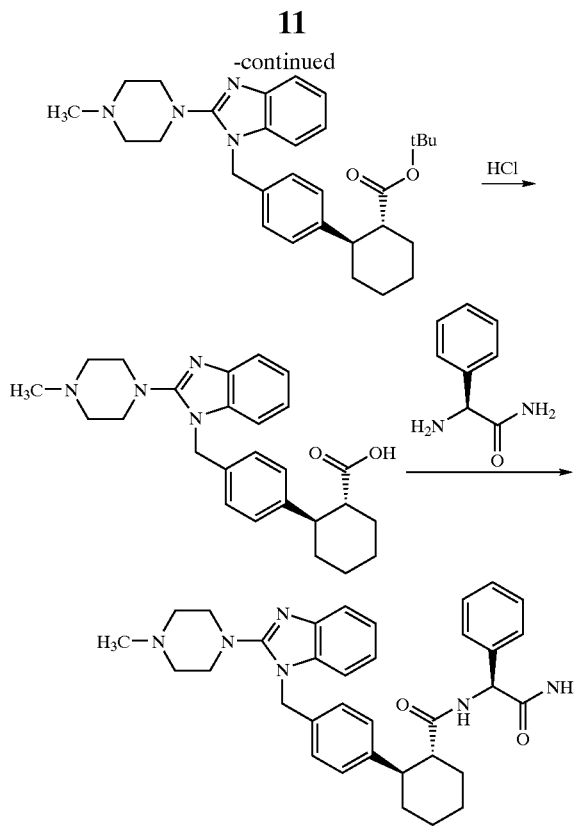

Suitable amino protective groups in the context of the invention are the customary amino protective groups used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxy-benzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxy-carbonyl, isopropoxycarbonyl, butoxycarbonyl, isobutoxycarbonyl, tert-butoxy-carbonyl, allyloxycarbonyl, vinyloxycarbonyl, 2-nitrobenzyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichloroethoxycarbonyl, 2,2,2-trichloro-tert-butoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl or 4-nitrophenyl. A preferred protective group for primary amines is phthalimide. Preferred protective groups for secondary amines are benzyloxycarbonyl and tert-butoxycarbonyl.

The amino protective groups can be removed in a manner known per se, for example under the hydrogenolytic, acidic or basic conditions, preferably using acids, such as, for example, hydrochloric acid or trifluoroacetic acid, in inert solvents, such as ether, dioxane and methylene chloride.

A suitable hydroxy protective group in the context of the definition given above is generally a protective group from the series: trimethylsilyl, triethylsilyl, triisopropylsilyl, tert-butyl-dimethylsilyl, dimethylthexylsilyl, tert-butyl-diphenylsilyl, trimethylsilylethoxycarbonyl, benzyl, triph-enylmethyl (trityl), monomethoxytrityl (MMTr), dimethyloxytrityl (DMTr), benzyloxycarbonyl, 2-nitrobenzyl, 4nitro-benzyl, 2-nitrobenzyloxycarbonyl, 4-nitrobenzyloxycarbonyl, tert-butyloxycarbonyl, 4-methoxybenzyl, 4-methoxybenzyloxycarbonyl, formyl, acetyl, trichloroacetyl, 2,2,2-trichloroethoxycarbonyl, 2,4dimethoxybenzyl, 2,4dimethoxybenzyl-oxycarbonyl, methoxymethyl, methylthiomethyl, methoxyethoxymethyl, [2-trimethylsilyl)ethoxy]-methyl, 2-(methylthiomethoxy) ethoxycarbonyl, tetra-hydropyranyl, benzoyl, N-succinimide, 4methylbenzoyl, 4-nitrobenzoyl, 4-fluorobenzoyl, 4-chlorobenzoyl or 4-methoxybenzoyl. Preference is given to tert-butyldimethylsilyl.

The hydroxy protective group can be removed in a manner known per se, for example using acid or base, or by addition of tetrabutyl ammoniumfluoride; or is carried out during the hydrolysis of the carboxylic acid.

Suitable solvents for the processes are customary organic solvents which do not change under the reaction conditions. These include ethers, such as diethyl ether, dioxane, terahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, tetrachloromethane, dichloroethylene, trichloroethylene or chlorobenzene, or ethyl acetate, pyridine, dimethyl sulphoxide, dimethylformamide, hexamethylphosphoric triamide, acetonitrile, acetone or nitromethane. It is also possible to use mixtures of the solvents mentioned. For the process [A] (II)+(III)→(IV), preference is given to diethyl ether, tetrahydrofuran and dimethylformamide. Particular preference is given to dimethylformamide.

Suitable for use as bases in the process according to the invention are, in general, inorganic or organic bases. These preferably include alkali hydroxides, such as, for example, sodium hydroxide or potassium hydroxide, alkaline earth metal hydroxides, such as, for examples barium hydroxide, alkali metal carbonates, such as sodium carbonate, potassium carbonate or caesium carbonate, alkaline earth metal carbonates, such as calcium carbonate, or alkali metal or alkaline earth metal alkoxides, such as sodium methoxide or potassium methoxide, sodium ethoxide or potassium ethoxide or potassium tert-butoxide, or organic amines (trialkyl ($C_1$-$C_6$)amines), such as triethylamine, or heterocycles, such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to use, as bases, alkali metals, such as sodium, or their hydrides, such as sodium hydride. Preference is given to sodium hydride, potassium carbonate, caesium carbonate, triethylamine, trimethylamine, pyridine, potassium tert-butoxide, DBU or DABCO. Very particularly preferred for the step [A](II)+(III)→(IV) is the use of sodium hydride.

In general, the bases are employed in an amount of from 0.05 mol to 10 mol, preferably from 1 mol to 2 mol, based on 1 mol of the compound of the formula (II).

The process (II)+(III)→(IV) according to the invention is generally carried out in a temperature range from −20° C. to +60° C., preferably from 0° C. to +60° C.

The process (II)+(III)→(IV) according to the invention is generally carried out under atmospheric pressure. However, it is also possible to carry out the process under elevated pressure or under reduced pressure (for example in a range from 0.5 to 5 bar.

The hydrolysis of the carboxylic esters is carried out by customary methods by treating the esters in inert solvents with customary bases, the salts which are formed initially being converted by treatment with acid into the free carboxylic acids, or, in the case of the t-butyl esters, with acid.

Suitable bases for the hydrolysis are the customary inorganic bases. These preferably include alkali metal hydroxides or alkaline earth metal hydroxides, such as, for example, sodium hydroxide, lithium hydroxide, potassium hydroxide or barium hydroxide, or alkali metal carbonates, such as sodium carbonate or potassium carbonate or sodium bicarbonate. Particular preference is given to using sodium hydroxide or lithium hydroxide.

Suitable acids are, in general, trifluoroacetic acid, sulphuric acid, hydrogen chloride, hydrogen bromide and acetic acid, or mixtures thereof, if appropriate with addition of water. Preference is given to hydrogen chloride or trifluoroacetic acid in the case of the tert-butyl esters and to hydrochloric acid in the case of the methyl esters.

Solvents which are suitable for the hydrolysis are water or organic solvents customarily used for hydrolysis. These preferably include alcohols, such as methanol, ethanol, propanol, isopropanol or butanol, or ethers, such as tetrahydrofuran or dioxane, dimethylformamide, dichloromethane or dimethyl sulphoxide. It is also possible to use mixtures of the solvents mentioned. Preference is given to water/tetrahydrofuran and, in the case or the reaction with trifluoroacetic acid, dichloromethane and, in the case of hydrogen chloride, tetrahydrofuran, diethyl ether or water.

The hydrolysis is generally carried out in a temperature range from 0° C. to +100° C.

In general, the hydrolysis is carried out at atmospheric pressure. However, it is also possible to operate under reduced pressure or under elevated pressure (for example from 0.5 to 5 bar).

When carrying out the hydrolyses, the base or the acid is generally employed in an amount of from 1 to 100 mol, preferably from 1.5 to 40 mol, based on 1 mol of the ester.

The carboxylic acids (V) are usually activated by being converted into the corresponding acyl halides, preferably acyl chlorides, or pre-activation with a customary condensing agent, which cam take place in situ or by isolating the activated carboxylic acid derivative. The acyl halides can be prepared by customary methods. The use of oxalyl chloride or thionyl chloride may be mentioned as an example.

Preferred auxiliaries used for the amide formations are condensing agents. Preference is given here to using the customary condensing agents, such as carbodiimides, for example N,N'-diethyl-, N,N'-dipropyl-, N,N'-diisopropyl-, N,N'-dicyclohexyl-carbodiimide, N-(3-dimethylaminoisopropyl)-N'-ethylcarbodiimide hydrochloride (EDC) or carbonyl compounds, such as carbonyldiimidazole, or 1,2-oxazolium compounds, such as 2-ethyl-5-phenyl-1,2-oxazolium-3-sulphate or 2-tert-butyl-5-methyl-isoxazolium perchlorate, or acylamino compounds, such as 2ethoxy-1-ethoxycarbonyl-1,2-dihydroquinoline, or propanephosphonic acid anhydride, or isobutyl chloroformate, or bis-(2-oxo-3-oxazolidinyl)-phosphoryl chloride or benzotriazolyloxy-tri(dimethylamino)phosphonium hexafluorophosphate and, as bases, alkali metal carbonates, for example sodium carbonate or bicarbonate and potassium carbonate or bicarbonate, or organic bases, such as trialkylamines, for example triethylamine, N-ethylmorpholine, N-methylpiperidine or diisopropyl-ethylamine. Particular preference is given to the combination of EDC. N-methylmorpholine and 1-hydroxybenzotriazole. Preferred solvents for the amide formation are dichloromethane and DMF.

The compounds of the general formulae (II), (IIIa), (VI) and (VII) are known or can be prepared by customary methods (cf. EP-A-0 725 061, EP-A-0 725 064).

Most or the compounds or the general formula (III) are novel, and they can be prepared, in the case that $R^{11}$ does not represent a heterocycle which is attached directly via N, by reacting compounds of the general formula (XI)

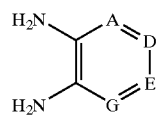

(XI), in which

A, D, E, G and $L^1$ are each as defined above with compounds of the general formula (XII)

  $R^{11}$—$CO_2H$ (XII)

in which $R^{11}$ is as defined above with removal of the water of reaction, if appropriate in the presence of an acid, preferably PPA, HCl and p-TsOH (cf. also *J. Org. Chem.* 1941. 6, 25 ff. and *Bull. Soc. Chem. Fr.* 1991, 128, 255–259)

and, in the case that $R^{11}$ represents one of the radicals listed above under $R^2$ which may optionally also carry a protective group, by converting compounds of the general formula (XI) initially by reaction with compounds of the general formula (XIII)

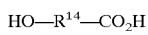 HO—$R^{14}$—$CO_2H$ (XIII)

in which $R^{14}$ represents $(C_1-C_8)$alkanediyl into compounds of the general formula (XIV)

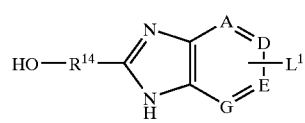

(XIV), in which

A, B, D, G, $R^{14}$ and $L^1$ are each as defined above in insert solvents, subsequently substituting the hydroxyl group by halogen, mesylate or tosylate, thus producing the compounds of the general formula (XV)

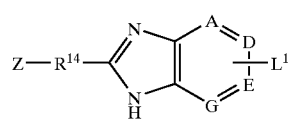

(XV)

in which $R^{14}$, A, D, E, G and $L^1$ are each as defined above and

Z represents halogen, mesylate or tosylate, and reacting these with amines of the general formula (XVI)

 $R^8R^9NH$ (XVI)

in which

R⁸ and R⁹ are each as defined above
(cf. also *J. Am. Chem. Soc.* 1948, 70, 3406; *J. Heterocycl. Chem.* 1969, 759–60).

Solvents which are suitable for the process are customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, triethylamine, pyridine, dimethyl sulphoxide, dimethylformamide, hexamethylphosphoric triamide, acetonitrile, acetone or nitromethane. It is also possible to use mixtures of the solvents mentioned. Preference is given to dichloromethane, tetrahydrofuran and dimethylformamide.

Bases suitable for use in the process according to the invention arc, in general, inorganic or organic bases. These preferably include alkali metal hydroxides, such as, for example, sodium hydroxide or potassium hydroxide, alkaline earth metal hydroxides, such as, for example, barium hydroxide, alkali metal carbonates, such as a; sodium carbonate, potassium carbonate or caesium carbonate, alkaline earth metal w carbonates, such as calcium carbonate, or alkali metal or alkaline earth metal alkoxides, such as sodium methoxide or potassium methoxide, sodium ethoxide or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to use, as bases, alkali metals, such as sodium, or their hydrides, such as sodium hydride. Preference is given to sodium hydride, potassium carbonate, triethylamine, trimethylamine, pyridine, potassium tert-butoxide, DBU or DABCO.

In general, the bases are employed in an amount of from 0.05 mol to 10 mol, preferably from 1 mol to 2 mol, based on 1 mol of the compound of the formula (XV).

The process according to the invention is generally carried out in a temperature range of from –50° C. to +100° C., preferably from –30° C. to +60° C.

The process according to the invention is generally carried out under atmospheric pressure. However, it is also possible to carry out the process under elevated pressure or under reduced pressure (for example in a range from 0.5 to 5 bar).

The compounds of the general formulae (XI), (XII), (XIII) and (XVI) are known per se or can be prepared by customary methods.

Some of the compounds of the general formulae (XIV) and (XV) are novel, and they can be prepared, for example, as described above.

The compounds of the general formulae (IV), (V), (VII), (IX) and (X) and their salts are novel and can be prepared as described above.

Surprisingly, the compounds of the general formula (I) according to the invention and their analogues have an unforeseeable useful pharmacological activity spectrum, combined with an improved solubility in water.

It has been found that the compounds according to the invention inhibit adenosine uptake.

They can be used orally or intravenously for the prophylaxis and treatment of cerebral ischaemia, stroke, reperfusion damage, brain trauma, oedema, spasms, epilepsy, respiratory arrest, cardiac arrest, Reye's syndrome, cerebral thrombosis, emboli, tumours, haemorrhages, encephalomyelitis, hydroencephalitis, spinal injuries, postoperative brain damage, injuries to the retina or the optical nerve after glaucoma, ischaemia, hypoxia, oedema or trauma and in the treatment of schizophrenia, sleep disturbances and pain.

Owing to their improved solubility in water, the compounds according to the invention are particularly suitable for intravenous administration.

Test Systems
1. Determination of the Solubility

To determine the solubility, a precipitation method was used:

10 mg of the test substance are completely dissolved in 50 µl of DMSO (stock solution). 20 µl of this solution are added to 2000 µl of physiological saline. This solution, in turn, is shaken at 25° C. in a Thermomixer Comfort (from Eppendorf) at 1400 rpm for 24 hours for equilibration.

The precipitated fractions of the test substance are centrifuged off using a Biofuge 15 from Heraeus at 14,000 rpm for 5 min. 1300 µl of the supernatant are once more centrifuged using a Microfuge from Beckmann at 45,000 rpm=125,000 g.

10 µl of this centrifigation supernatant are then diluted with 1000 µl of DMSO, and this solution is measured by HPLC (Hewlett Packard 1090, method, gradient from 100% PBS buffer pH=4 to 10% buffer/90% acetonitrile over a period of 15 min, column: RPl8; PBS buffer pH=4 is a physiological saline solution adjusted to pH=4 using phosphate buffer).

Using a calibration curve, the measured peak area of the HPLC measurement is converted into substance concentration. For the calibration curve, 20 µl of the stock solution are diluted successively with DMSO such that 5 concentrations of 2.5 mg/l to 2000 mg/l result. These solutions are likewise measured by HPLC (see method above), and the peak areas are plotted as a function of the concentrations.

The solubility, determined by this method, of Examples 3 and 5 is 176 and 16 mg/l, respectively.

2. Binding of the Compounds According to the Invention to an Adenosine Transport Protein From Calf Cortex The ability of substances to influence the adenosine uptake system is investigated firstly by determining the binding affinity of selected substances to an adenosine transport protein of the CNS and secondly by determining the inhibiting effect of the substances on functional adenosine uptake.

For the binding test, a membrane preparation of cerebral calf cortex is used, which expresses the relevant adenosine transporter. The binding affinity ($K_i$ value) is determined by measuring the displacement of a specific radio-labelled ligand [nitrobenzylthioinosine (NBTI)] from the binding site in question by test substances. The binding site is the binding site on the transport protein which is relevant for the actual transport process. Thus, binding of test substances in this experiment results in a quantifiable release of bound radioactive NBTI which makes determination of the $K_i$ value possible. (*J. Neurochemistry* 1982,39, 184–191).

Examples 3 and 5 inhibit NBTI-binding, in each case with $K_i$=2 nM.

3. Inhibition of Adenosine Uptake in Calf Cortex Synaptosomes by Compounds According to the Invention For the functional adenosine uptake test, a synaptosome preparation from cerebral calf cortex is used which expresses the adenosine transporter in question. Synaptosomes are cell-free, functionally active vesicles which are obtained from cortex tissue using sheer forces and which still have the properties of an intact synaptic knob. The inhibitory activity ($IC_{50}$ value) is determined by measuring the inhibition of the uptake of the specific radio-labelled "substrate" adenosine into the synaptosomes (*J. Neurochemistry* 1990, 55, 541–550).

Examples 3 and 5 inhibit adenosine uptake into synaptosomes with $IC_{50}$=8 nM and 14 nM, respectively.

The neuroprotective activity of the compounds according to the invention was determined in the animal model of transient occlusion of the middle cerebral artery (tMCA-O) and the subdural haematoma (SDH).

4. tMCA-O

This rodent model (rat) imitates the pathophysiology and cerebral pathology of stroke or circulatory arrest (embolization, thrombosis, vaso spasm, cardiac arrest, rapidly and dramatically reduced blood pressure, high blood loss, etc.) with subsequent recirculation in man (modified according to: *J. Cereb. Blood Flow Metab.* 1997, 17, 1066–1073).

Under general anaesthesia (inhalation anaesthesia with isoflurane), the hairs in the lower anterior neck region are shaved off, in the dorsal position, the head is fixed, the skin is disinfected and the neck area is opened in the middle along the trachea. The right lateral neck muscles are severed bluntly and, together with the skin, pulled to the side (retractors) so that the common carotid artery is clearly visible. The common carotid artery is exposed towards the head up to the point where it branches into the internal carotid artery and the external carotid artery. Using surgical suture material, the common carotid artery (near the thorax) and the external carotid artery are tied off. Using a microclamp; the internal carotid artery is closed temporarily. The common carotid artery is opened, and a nylon monofilament with a rounded tip and a silicone cylinder of a length of 1 cm are passed through the common carotid artery and, after opening of the microclamp; further through the internal carotid artery, to close the exit of the middle cerebral artery. Using two temporary suture loops, the filament is fixed in the internal carotid artery. Alter one hour, the filament is pulled out, and the internal carotid artery and the common carotid artery are tied off above the opening. Blood is supplied via the contralateral muscular system.

Substance administration is begun directly with the start of reperfusion. The operation wound is surgically looked after. During the operation and the administration of the substance (infusion), the body temperature is kept constant using a heating plate.

After 2 days of post-operative survival, the volume of the cerebral infarct is determined with the aid of a computer-supported image analysis system using preproduced series of histological brain sections. The size of the infarct is evaluated differentially by cortex, striatum, hippocampus and other brain areas.

At a dose of 0.001 mg/(kg×h) (i.v. infusion), Examples 3 and 5 reduce the infarct volume by 81 and 91%, respectively, in comparison to control animals.

5. Subdural Haematoma in Rats (SDH)

This rodent model (rat) imitates pathophysiology and cerebral pathology of the blunt skull-brain trauma with subdural hemorrhage and development of a subdural haematoma in man. (*Neurosurgery* 190, 27,433–439).

Under anaesthesia, the animals are unilaterally injected subdurally with their own blood. Under the haematoma, an infarct forms. The substance is administered according to different schedules and via different administration routes (i.v., i.p.). The size of the infarct is determined as described in the model of the transient focal ischaemia in rats (tMCA-O).

At a dose of 0.001 mg/(kg×h) (i.v. infusion), Examples 3 and 4 reduce the infarct volume by 30 and 45%, respectively, in comparison to control animals.

The novel active compounds can be converted in a known manner into the customary formulations, such as tablets, coated tablets, pills, granules, aerosols, syrups, emulsions, suspensions and solutions, using inert, nontoxic, pharmaceutically suitable carriers or solvents. In this case the therapeutically active compound should in each case be present in a concentration of about 0.0001 to 900% by weight, preferably 0.0001 to 1.0% by weight, of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, if the diluent used is water, organic solvents can optionally be used as auxiliary solvents.

Administration is carried out in a customary manner, preferably orally, transdermally or parenterally, in particular perlingually or intravenously.

In general it has proven advantageous in the case of intravenous administration to administer amounts of approximately 0.00001 to 10 mg/kg, preferably approximately 0.0001 to 1 mg/kg, of body weight to achieve effective results.

In spite of this, if appropriate, it may be necessary to depart from the amounts mentioned, namely depending on the body weight or the type of administration route, on the individual response to the medicament, the manner of its formulation and the time or interval at which administration takes place. Thus, in some cases it may be adequate to manage with less than the abovementioned minimum amount, while in other cases the upper limits mentioned must be exceeded. In the case of the administration of relatively large amounts, it may be advisable to divide these into several individual doses over the course of the day.

| Abbreviations | |
|---|---|
| DMF: | N,N-dimethylformamide |
| DMSO: | dimethyl sulphoxide |
| PPA: | polyphosphoric acid |
| TFA: | trifluoroacetic acid |
| THF: | tetrahydrofuran |

Starting Materials

EXAMPLE 1A (1R, 2R-23-(4-Methyl-phenyl)-cyclohexane-1-carboxylic acid

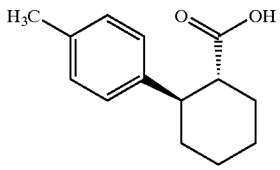

Racemic (1R*,2R*,)-2-(4-methyl-phenyl)-cyclohexane-1-carboxylic acid was prepared analogously to the pus described in U.S. Pat. No. 5,395,840, column 16. The resulting racemic material was separated into the enantiomers using the following procedure.

The racemic acid (415 g; 1.9 mol) and triethylamine (96.2 g; 0.95 mol; 131.8 ml) were suspended in a mixture of THF (2.7 l) and water (5.3 l). At 60° C., S-(−)-phenylethylamine (115.2 g; 0.95 mol) was added dropwise, resulting in a precipitate being formed. The mixture was stirred at 60° C. for 2 h and then cooled using an ice-bath. The precipitate was filtered off with suction, giving predominantly the phenylethylamine salt of the (1S,2S)-enantiomer. The filtrate was acidified using conc. HCl and extracted twice using dichloromethane. The combined extracts were dried over sodium sulphate and concentrated. Yield: 202.4 g (28%) of a mixture of enantiomers enriched with the (1R,2R)-isomer.

This mixture was treated with R-(+)-phenylethylamine as described above to precipitate the desired enantiomer as a salt. The colourless crystals were filtered off with suction and recrystallized from acetonitrile/methanol (6:1). X-ray analysis of these crystals confirmed the (1R, 2R)-configuration. Yield 136.9 g (46%). Work-up (see above) gave 89 g of (1R, 2R)-2-(4-methylphenyl)-cyclohexane-1-carboxylic acid.

EXAMPLE 2A

Tert-Butyl (1R, 2R)-2-(4-bromomethyl-phenyl)-cyclohexane-1-carboxylate

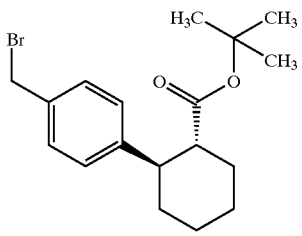

The intermediate was prepared analogously to the procedure for the racemate (U.S. Pat. No. 5,395,840, column 17). For purification, the resulting mixture was stirred with diethyl ether.

EXAMPLE 3A 2-(2-Phthalimidylethyl)-benzimidazole

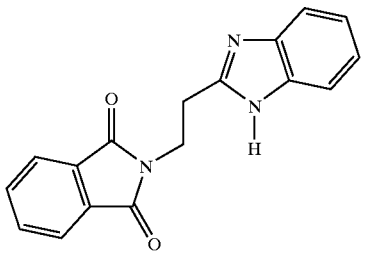

2-Aminoethylbenzimidazole dihydrochloride (*Bull. Soc. Chem. Fr.* 1991, 128, 255–259; 2.34 g, 10 mmol), phthalic anhydride (1.63 g. 11 mmol) and triethylamine (2.79 ml, 20 mmol) in chloroform (25 ml) were heated at reflux overnight , and the mixture was then cooled to room temperature, diluted with ethyl acetate and filtered off. The filtrate was washed with saturated sodium carbonate solution, buffer (pH=7) and saturated sodium chloride solution and dried over sodium sulphate. Chromatography (dichloromethane:methanol 10:1, $R_f$=0.4) gave 2.08 g of 2-(2-phthalimidylethyl)benzimidazole (71.4% of theory) as a colourless foam. MS (DCl, $NH_3$)=292 (M+H$^+$). $^1$H-NMR (DMSO-$d_6$): 3.15 (2H, t); 4.0 (2H, t); 7.05–71 (2H, m); 7.4–7.5 (2H, m); 7.8–7.9 (4H, m); 12.4 (1H, br s).

The remainder of the synthesis is carried out following the general procedures A, B and C as mentioned below, and in the last step, the phthalimide group is cleaved off as described below.

EXAMPLE 4A 2-(2-Hydroxyethoxymethyl)-pyrido[2,3-d]imidazole

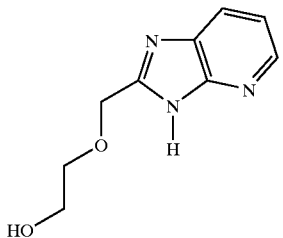

1,4-Dioxan-2-one (6.13 g, 60 mmol) and 2,3-diaminopyridine (5.46 g, 50 mmol) in mesitylene (100 ml) were heated at reflux in a Dean-Stark separator for 10 h. After cooling, mesitylene was decanted off and the residue was purified by silica gel chromatography (dichloromethane:methanol 9:1) (yield: 8.47 g, 87% of theory).

MS(DCl)=194 (M+H, 100%); $^1$H-NMR (DMSO-$_6$): 3.78 (2H, m); 3.89 (2H, m); 4.91 (2H, s); 5.3 (1H,s); 7.18 (1H, dd); 7.95 (1H, d); 8.43 (1H, dd); 12.7 (1H, br s).

EXAMPLE 5A

2-[2-(tert-Butyldimethylsilyloxy)ethoxymethyl]-pyrido[2,3-d]imidazole

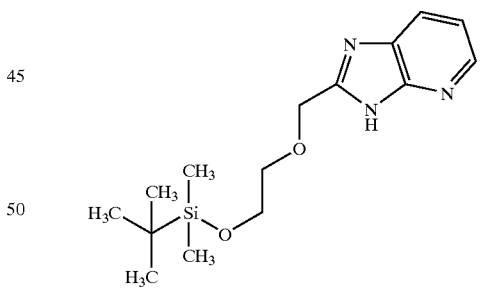

8.4 g (43.48 mmol) of 2-(2-hydroxyethoxymethyl)-(pyrido-[2,3]-1H-imidazole) and 4.84 g (47.82 mmol) of triethylamine were dissolved in 120 ml of DMF and admixed with 7.21 g (47.8 mmol) of TBDMS chloride, the mixture warming to about 40° C. Stirring at room temperature was continued for 2 h, and the mixture was then poured into water, giving the product in crystalline form. The product was filtered off with suction, washed with a little water and dried under high vacuum. $^1$H-NMR (DMSO-$d_6$): 0.02 (6H, s); 0.83 (9H, s); 3.52 (2H, t); 3.75 (2H, t); 4.73 (2H, s); (1H, dd); 7.90 (1H, dd); 8.43 (1H, dd); 12.9 (1H, br s).

EXAMPLE 6A 2-tert-Butyldimethylsilyloxymethyl-benzimidazole

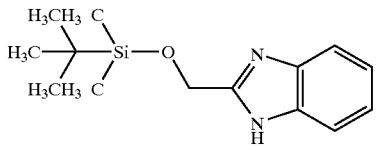

At room temperature, triethylamine (2.27 ml, 163 mmol) and TBDMS chloride (1.65 g, 10.95 mmol) were added to a solution of 2-hydroxymethylbenzimidazole (1.4 g, 9.95 mmol) in DMF (30 ml). After 3.5 h, the reaction was terminated by addition of water, the mixture was extracted with diethyl ether and the organic phase was dried over sodium sulphate. Chromatography (silica gel, cyclohexane-:ethyl acetate 2:1, $R_f$=0.35) gave 2.52 g of 2-tert-butyldimethylsilyloxymethylbenzimidazole (97% of theory) as a brownish powder. MS (DCl, $NH_3$)=263 (M+H$^+$). $^1$H-NMR (DMSO-d$_6$): 0.00 (6H, s); 0.80 (9H, s); 4.75 (2H, s); 7.0–7.1 (2H, m); 7.4–7.5 (2H, m); 12.15 (1H, br s).

EXAMPLE 7A 2-(2-Hydroxyethoxymethyl)-benzimidazole

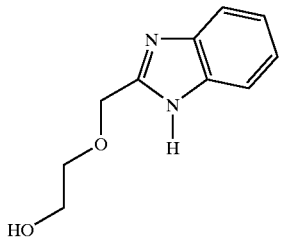

Using a Dean-Stark separator, 1.4-dioxan-2-one (204 g, 20 mmol) and 1.2-diaminobenzene (2.16 g, 20 mmol) were heated under reflux in mesitylene (150 ml) for 10 h. The crystals formed on cooling were then filtered off with suction (2.94 g. 77% of theory). $R_f$ (dichloromethane:methanol 10:1)=0.45, MS (EI)=192 (M$^+$, 20%), 148 (20%), 147 (40%), 132 (100%), $^1$H-NMR (DMSO-d$_6$): 3.6 (4H, s); 4.65 (1H, s); 4.7 (2H, s); 7.1–7.2 (2H, m); 7.45 (1H, d); 7.55 (1H, d); 12.4 (1H, br s).

General Alkylation Procedure [A]

In a typical batch, sodium hydride (6.3 mmol) was, at 0° C., added to absolution of the imidazole of the general formula (III) (6 mmol) in dry DMF (30 ml). After 30 min at room temperature and 30 min at 40° C., the compound of the general formula (II) (6.3 mmol) was added at 0° C., and the reaction mixture was stirred at room temperature overnight. The reaction was then terminated by addition of water, the mixture was extracts with diethyl ether and the organic phase was then dried over sodium sulphate Chromatography (silica gel, cyclohexane:ethyl acetate) gave the product in a yield of 60–70%.

General Procedure for Ester Hydrolysis [B]

In a typical batch, trifluoroacetic acid (5 ml) was added at room temperature to a solution of the ester of the general formula (IV) (T=tert-Bu; 1.5 mmol) in dichloromethane (5 ml). After 2 h, the mixture was cooled to 0° C., adjusted to pH=2 using aqueous sodium hydroxide solution (about 30 ml, 2M) and extracted with dichloromethane. Drying of the organic phase over sodium sulphate gave, after concentration, the compound of the general formula (V).

General Procedure for Amide Formation [C]

A suspension of acid (V) (4 mmol), (S)-phenylglycinamide hydrochloride (4.2 mmol), 1-hydroxybenzotriazole (4.4 mmol), EDC hydrochloride (4.8 mmol) and triethylamine (12 mmol) in dichloromethane (40 ml) was stirred at room temperature for 24–48 h. Water was added, and the mixture was then extracted with dichloromethane (in some cases with methanol) and the organic phase was dried over sodium sulphate (or magnesium sulphate) and chromatographed (silica gel, dichloromethane:methanol). This gave the desired product in a yield of 60–80%.

Analogously to procedure C, it is possible to employ phenylglycinol instead of phenylglycinamide.

PREPARATION EXAMPLES

EXAMPLE 1

(S)-N-{(1R*, 2R*)-{4-[2-(2-Aminoethyl-benzimidazol-1-yl)methyl]phenyl}-cyclohex-2-yl-carbonyl}-phenylglycinamide

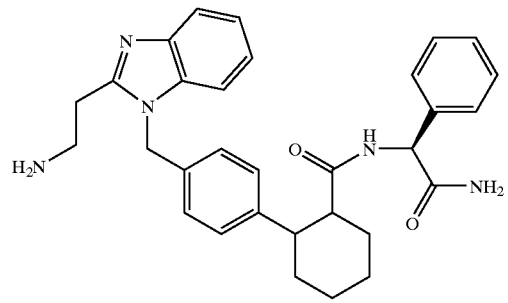

A suspension of (2S-N-[(2R*)-(4-{2-(2-phthaloylaminoethyl)-benzimidazol-1-yl-methyl}-phenyl)-cyclohexyl-(1R*)-carbonyl]-phenylglycinamide (prepare according to the general procedures [A–C] from the compound of Example 3A and the racemate of Example 2A according to U.S. Pat. No. 5,395,840, Example IV; 500 mg, 0.78 mmol, mixture of diastereomers) in ethanol (25 ml) was admixed with hydrazine hydrate (0.38 ml, 7.82 mmol). The mixture was stirred at room temperature overnight and then adjusted to pH=2 using hydrochloric acid (1M) and concentrated. Partition between 10% aqueous sodium bicarbonate solution and dichloromethane, drying of the organic phase over sodium sulphate and chromatography (silica gel, dichloromethane:methanol:conc. aqueous ammonia 100:13:1.3, Rf(10:1:0.2)=0.1) gave the title compound (292 mg, 72%, mixture of diastereomers) as a yellowish powder. MS (DCl, $NH_3$)=510 (M+H$^+$). $^1$H-NMR (DMSO-d$_6$): 1.2–1.5 (4H, m); 1.6-1.9 (4H, m); 2.0 (2H, br s); 2.6-3.0 (6H, m); 5.1–5.2 (A:1H, d; B:1H, d); 5.4–5.5 (A:2H, s; B:2H, s); 6.85–7.0 (4H, m); 7.1–7.3 (7H, m); 7.4–7.5 (1H, m); 7.55–7.65 (4H, m); 8.05–8.15 (A:1H, d; B:1H, d).

EXAMPLE 2

(S)-N-{(1R, 2R)-{4-{[2-(2-Aminoethyl)-benzimidazol-1-yl)methyl}phenyl}-cyclohex-1-yl-carbonyl}phenylglycinamide dihydrochloride

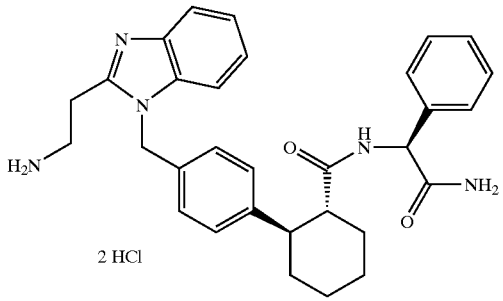

2 HCl

Chromatographic separation of the starting material from Example 1 (silica gel, methylene chloride:methanol) gave diastereomerically pure (S)-(N)-{(1R, 2R)2-{4-{2-[2-(phthaloyl-amino)-ethyl]-benzimidazol-1-yl}methyl}-phenyl}-cyclohex-1-yl-carbonyl-phenylglycinamide which was deprotected analogously to Example 1 and then dissolved in as small amount of dichloromethane as possible, treated with approximately 2 equivalents of 1M HCl in diethyl ether and concentrated. Found: C 64.21 H 6.58 Calc.: C 63.91 H 6.49

EXAMPLE 3

(S)-N-{{(1R, 2R-{4-{2-[2-(Morpholine-4-yl-methyl)-1H-pyrido[2,3-d]imidazol-1-yl]methyl}-phenyl}-cyclohex-1-yl}carbonyl}-phenylglycinamide

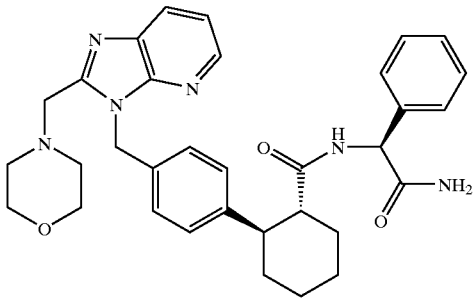

a) 2-Hydroxymethyl-1H-pyrido[2,3-d]imidazole

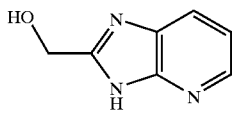

using a Dan-Stark separator, 2,3-diaminopyridine (54.6 g; 0.5 mol) and glycolic acid (38 g; 0.5 mol) in 700 ml of mesitylene were boiled under reflux until the calculated amount of water had separated off. The mixture was then cooled to room temperature, and the resulting precipitate was filtered off with suction and, with addition of activated carbon, boiled in 800 ml of water for 15 min. The hot suspension was filtered and once more cooled to room temperature, and the colourless crystals that precipitated out were filtered off with suction and dried. Yield: 56.4 g (75%).

b) 2-Chloromethyl-1H-pyrido[2,3-d]imidazole hydrochloride:

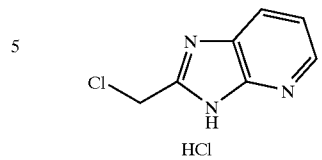

The compound from Example 3a (14.9 g; 100 mmol) was suspended in 25 ml of ethanol, and a stream of dry HCl was introduced until the mixture was saturated. The resulting hydrochloride was filtered off with suction and dried under reduced pressure. Yield 18.1 g (100%). This was suspended in 100 ml of chloroform and mixed with 35 ml of thionyl chloride. The mixture was then heated under reflux for 24 h and filtered whilst still hot, and the precipitate was washed with chloroform and dried under reduced pressure. Yield 18.9 g (92%).

c) 2-Morpholin-4-yl-methyl)-1H-pyrido[2,3-d]imidazole:

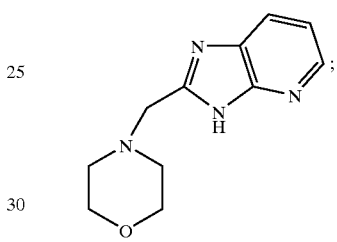

The compound from Example 3b (13.7 g; 67 mmol) and morpholine (28.6 g; 328 mmol) were boiled under reflux for 3 h. The mixture was concentrated and the residue was taken up in sodium bicarbonate solution. This suspension was, with addition of activated carbon, boiled for 15 min and subsequently filtered whilst still hot. The mixture was concentrated and the resulting product was then purified by column chromatography (silica gel (70–230 mesh ASTM); mobile phase: 100:30:1 ethyl acetate ethanol/triethylamine). The product can be recrystallized from ethyl acetate/hexane.

d) tert-Butyl(1R, 2R)-{4-{[2-(morpholin-4-yl-methyl)-1H-pyrido[2,3-d]imidazol1yl]methyl}-phenyl}-cyclohexane-1-carboxylate

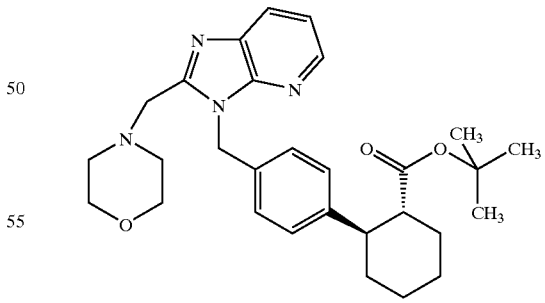

Under argon, a 60% strength suspension of sodium hydride in oil (2 g; 51.6 mmol) was suspended in 150 ml of DMF, and the compound from Example 3c (9.5 g; 43.5 mmol) was added. The mixture was heated at 50° C. for 30 min, and a precipitate formed. The mixture was then cooled to room temperature and the compound from Example 2A (17.3 g; 44 mmol) was added, and the mixture was then stirred at room temperature for 20 h. The resulting clear solution was concentrated under high vacuum and the residue was taken up in dichloromethane/water. The organic phase was separated off, dried over sodium sulphate and concentrated. The residue was then purified by column chromatography (silica gel (70–230 mesh ASTM); mobile phase: 100:4 dichloromethane/methanol). Yield 10 g (47%) of a brown viscose oil.

e) (1R,2R)-2-{4-{[2-(Morpholin-4-yl-methyl)-1H-pyrido[2,3-d]imidazol-1-yl]methyl}phenyl}cyclohexane-1-carboxylic Acid

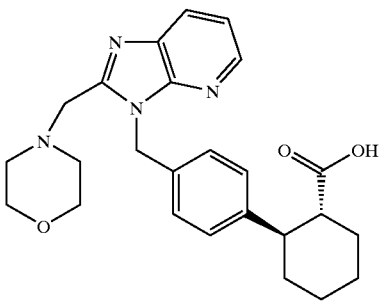

The compound from Example 3d (10 g, 20.4 mmol), 120 ml of dichloromethane and 100 ml of trifluoroacetic acid were stirred at room temperature for 1 h. With cooling, the mixture was then neutralized with conc. aqueous sodium hydroxide solution and the org. phase was separated off, dried and concentrated. The residue was purified by column chromatography (mobile phase: dichloromethane/methanol 100:6). Yield 7.3 g (80%) of a colourless amorphous solid.

f) (S)-N-{{(1R,2R)-2-{4-{[2-(Morpholin-4-yl-methyl)-1H-pyrido[2,3-d]imidazol-1-yl]methyl}-phenyl}-cyclohex-1-yl}carbonyl}-phenylglycinamide

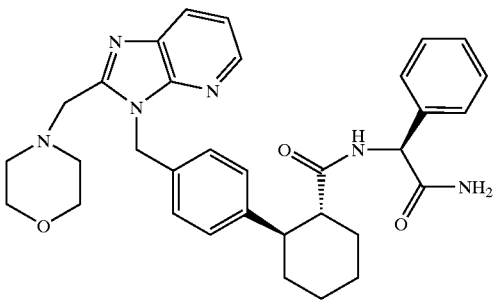

According to the general process [C], the compound from Example 3e (1.4 g; 3.22 mmol) was reacted with addition of a spatular tip of DMAP (4-dimethylaminopyridine). For work-up, the product was extracted with dichloromethane and purified by column chromatography (dichloromethane/methanol 100:6). Yield 1.7 g (93%) of a pale yellowish powder.

$^1$H-NMR (300 MHz; CDCl$_3$) δ [ppm]: 1.25–1.5 (3H; br m), 1.62 (1H; dq), 1.8 (3H; m), 1.94 (1H; dd), 2.31 (1H; dt), 2.42 (4H, br m), 2.67 (1H; dt), 3.61 (6H; m), 5.21 (1H; d), 5.49 (1H, br s), 5.63 (2H; d+d), 5.72 (1H; br s), 6.41 (1H; d), 6.82 (2H; d), 6.92 (2H; d), 6.98 (2H; d), 7.13 (2H, t), 7.18 (1H; t), 7.23 (1H; dd), 8.03 (1H; d), 8.42 (1H; d); MS (DCl/NH3)[m/z]: 567 (100, M+H).

EXAMPLE 4

(S)-N-{{(1R,2R)-2-{4-{2-[2-(Morpholin-4-yl-methyl)-1H-pyrido[2,3-d]imidazol-1-yl]methyl}-phenyl}-cyclohex-1-yl}carbonyl}-phenylglycinamide hydrochloride The compound from Example 3 was completely dissolved in as small an amount of dichloromethane as possible and treated with approximately 2 equivalents of 1M-HCl in diethyl ether. The resulting precipitate was filtered off with suction [m.p. 158° C. (decomp.)].

EXAMPLE 5

(S)-N-{{(1R,2R)-2-{4-{[2-(4-Methyl-piperazin-1-yl)benzimidazol-1-yl]methyl}-phenyl}-cyclohex-1-yl}carbonyl}-phenylglycinamide a) tert-butyl(1R,2R)-2-{4-[(2-Chloro-benzimidazol-1-yl)methyl]-phenyl}-cyclohexane-1-carboxylate

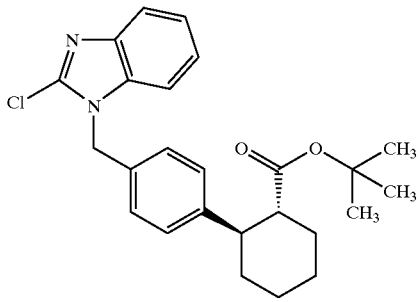

According to the general procedure [A], the title compound was prepared from 2-chlorobenzimidazole and the compound from Example 2A [R$_f$ (cyclohexane:ethyl acetate=1:1)=0.85].

b) (1,R2)-2-{4-{[2-(4-Methyl-piperazin-1-yl)-benzimidazol-1-yl]methyl}-phenyl}-cyclohexane-1-carboxylic acid

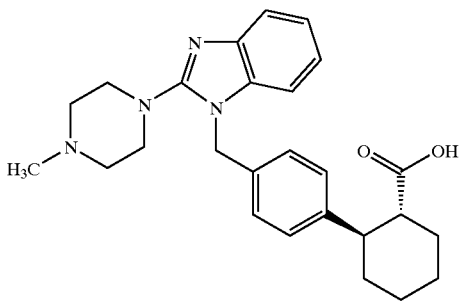

A solution of the compound from Example 5a (34.0 g, 56.0 mmol) in N-methylpiperazine (77.7 ml, 700 mmol) was heated at 100° C. overnight and then concentrated and chromatographed (silica gel, dichloromethane:methanol=20:1 to 10:1, R$_f$ (10:1)=0.32). This gave 32.0 g of tert-butyl (1R,2R)-2-{4-{[2-(4-methyl-piperazin-1-yl)-benzimidazol-1-yl]methyl}-phenyl}-cyclohexan-1-carboxylate which were reacted at room temperature with hydrochloric acid (180 ml, 6M) overnight. The reaction mixture was washed at pH=7 with dichloromethane and the organic phase was dried over magnesium sulphate and chromatographed (silica gel, dichloromethane:methanol 5:1, R$_f$=0.13), giving 19 g (78% of theory over 2 steps) of the title compound. MS (ESI) 433 (M+H$^+$). $^1$H-NMR (DMSO-d$_6$):1.35–1.5 (4H, m); 1.65–1.8 (3H, m); 1.9–2.0 (1H, m); 2.2 (3H, s); 2.4–2.5 (5H, m); 2.6–2.7 (1H, m); 3.15 (4H, ψt); 3.4 (1H, very br s); 5.2 (2H, s); 7.0–7.2 (7H, m); 7.4 (1H, d).

c) (S)-N-{{(1R,2R)-2-{4-{[2-(4-Methyl-piperazin-1-yl)-benzimidazol-1-yl]methyl}-phenyl}-cyclohex-1-yl}-carbonyl}-phenylglycinamide

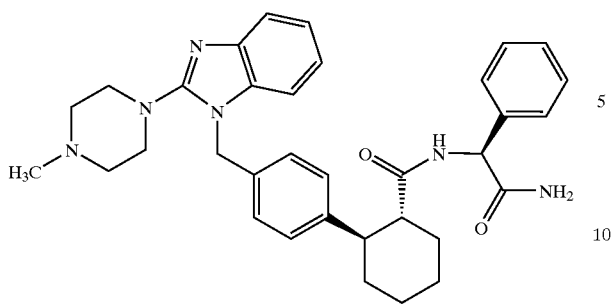

A suspension of the compound from Example 5b (19 g, 43.9 mmol), (S)-phenylglycinamide hydrochloride (8.61 g, 46.1 mmol), 1-hydroxybenzotriazole (7.68 g, 483 mmol), EDC hydrochloride (9.68 g, 50.5 mmol) and triethylamine (24.5 ml, 175.7 mmol) in dichloromethane (1000 ml) was stirred at room temperature over the weekend. Water was added, the mixture was then extracted with dichloromethane methanol and the extract was dried over magnesium sulphate and concentrated. The slightly yellowish solid was stirred in dichloromethane/methanol (10:1, 220 ml) and the clean title compound was filtered off with suction and dried under reduced pressure at 40° C. (14.5 g, 59%), $R_f$ (dichloromethane:methanol 10:1)=0.30. MS (4DCl, $NH_3$)= 565 (M+H$^+$). $^1$H-NMR (DMSO-d$_6$): 1.2–1.5 (4H, m); 1.6–1.85 (4H, m); 2.2 (3H, s); 2.45 (4H, ψt); 2.65 (1H, br t); 2.8 (1H, td); 3.15 (4H, ψt); 5.15 (1H, d), 5.2 (2H, s); 6.9 (2H, d); 6.95–7.2 (11H, m); 7.45 (1H, d); 7.6 (1H, br s); 8.0 (1H, d).

EXAMPLE 6

(S)-N-{{(1R,2R)-2-{4-{[2-(4-Methyl-piperazin-1-yl)-benzimidazol-1-yl]methyl}-phenyl}-cyclohex-1-yl}carbonyl}-phenylglycinamide hydrochloride

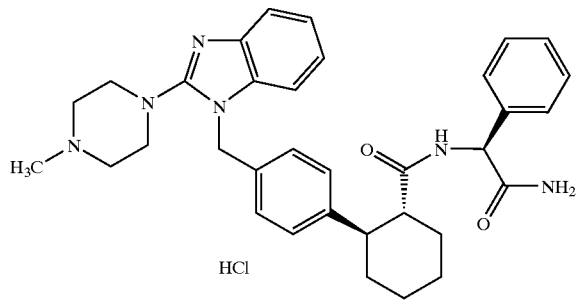

HCl

The compound from Example 5 (100 mg, 0.177 mmol) was dissolved in dichloromethane/methanol (2.5.1; 5 ml) and admixed with 1M HCl/diethyl ether (0.177 mmol), and the mixture was stirred for 5 minutes and then concentrated under reduced pressure in the cold. The title compound was obtained as a colourless powder (106 mg) m.p. 200° C. (decomp.).

The Examples 7 to 10 listed in Table 1 below were prepared analogously to Example 5, using the corresponding substituted peperazines.

TABLE 1

| Ex. No. | Structure | $R_f$* |
|---|---|---|
| 7 | ![structure] | 0.3 (10:1:0) |
| 8 | ![structure] | 0.3 (10:1:0.1) |

TABLE 1-continued

| Ex. No. | Structure | $R_f$* |
|---|---|---|
| 9 | 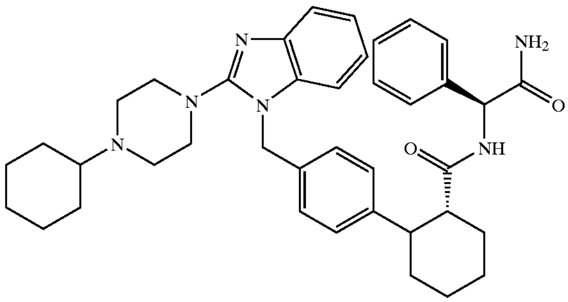 | 0.4 (10:1:0.1) |
| 10 | 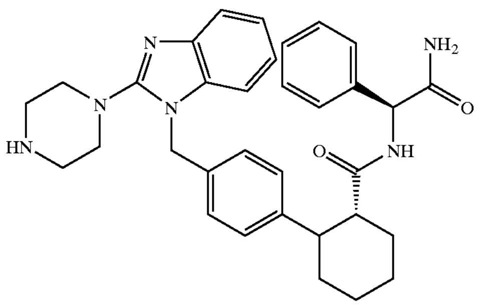 | 0.3 (10:1:0.1) |

*CH$_2$Cl$_2$:methanol:conc. ammonia

The examples 11 and 12 listed in Table 2 below are prepared according to the general procedures A, B and C, starting with the compound from Example 6A.

TABLE 2

| Ex. No. | Structure | $R_f$* |
|---|---|---|
| 11 | 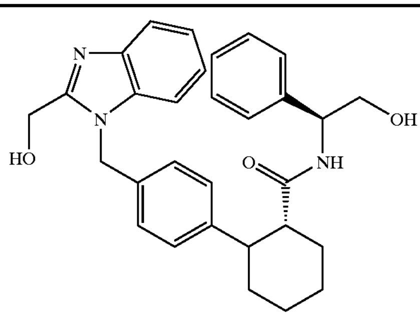 | 0.4 (10:1) |
| 12 | 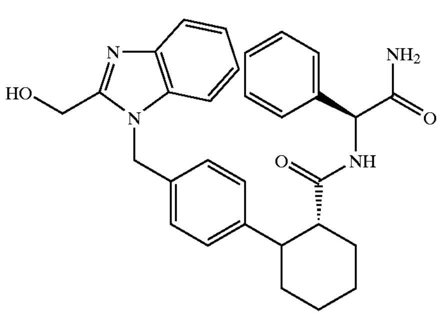 | 0.35 (10:1) |

*CH$_2$Cl$_2$:methanol

EXAMPLE 13

(S)-N-{{(1R,2R)-2-{4-{[2-(2-Hydroxyethoxy)methyl]-benzimidazol-1-yl}methyl}-phenyl}-cyclohex-1-yl}carbonyl}-phenylglycinamide

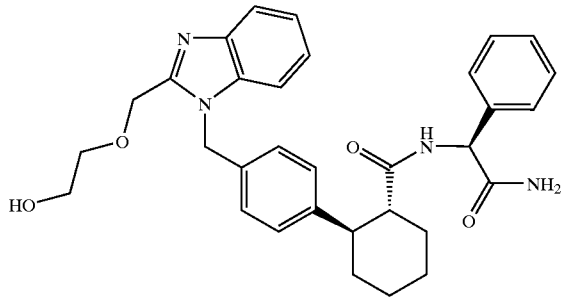

Starting from the compound of Example 7A which is silylated with TBDMS chloride analogously to Example 6A and then reacted according to the general procedures A, B and C, the title compound is obtained.

$R_f$ (dichloromethane:methanol 20:1)=0.20. MS (ESI)= 541 (M+H$^+$). $^1$H-NMR (DMSO-d$_6$): 1.2–1.5 (4H, m); 1.6–1.9 (4H, m); 2.6–2.7 (1H, m); 2.75–2.85 (1H, m); 3.5 (4H, s); 4.65 (1H, br s); 4.6 (2H, s); 5.15 (1H, d); 5.55 (2H, s); 6.9 (2H, d); 6.95–7.2 (10H, m); 7.45 (1H, m); 7.6 (1H, s); 7.65 (1H, m); 8.05 (1H, d).

Examples 14 to 16 listed in Table 3 below are prepared analogously to Example 13 from the appropriate starting materials.

TABLE 3

| Ex. No. | Structure | $R_f$ (CH$_2$Cl$_2$:MeOH: conc. ammonia) | MS |
|---|---|---|---|
| 14 | 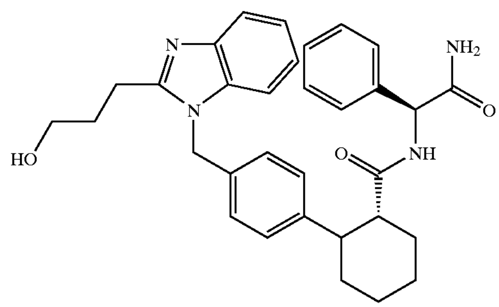 | 0.44 (10:1:0) | |
| 15 | 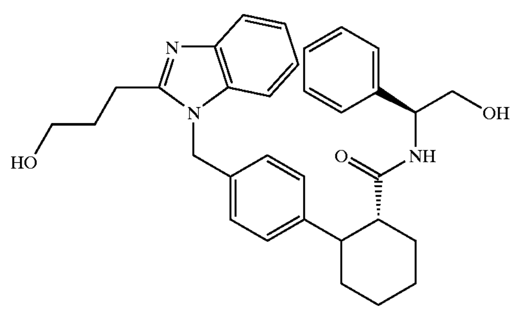 | 0.46 (10:1:0) | |
| 16 | 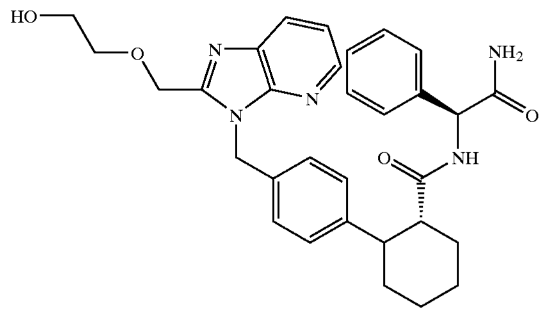 | | EI: 541 (M+) |

What is claimed is:

1. A compound of the formula (I)

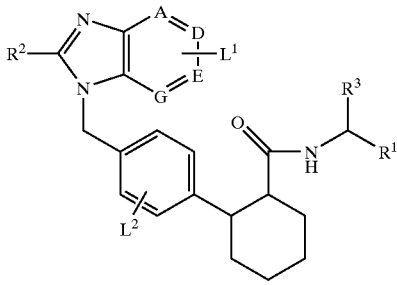

in which

A, D, E, and G each represents CH, $L^1$ and $L^2$ are identical or different and independently of one another each represents one or more radicals selected from the group consisting of hydrogen, halogen, hydroxyl, carboxyl, cyano, nitro, trifluoromethyl, trifluormethoxy, $(C_1-C_6)$-alkyl, $(C_1-C_6)$-alkoxy and $(C_1-C_6)$-alkoxy-carbonyl, $R^1$ represents a radical of the formula $CO-NR^4R^5$ in which
$R^4$ and $R^5$ are identical or different and each represents hydrogen or $(C_1-C_6)$-alkyl, $R^2$ represents a 4-$R^7$-piperazin-1-yl radical,
which is optionally substituted by one to three hydroxyl groups and/or by a radical of the formula $-NR^8R^9$
in which
$R^7$ represents hydrogen, $(C_1-C_6)$-alkyl, hydroxy-$(C_1-C_6)$-alkyl or $(C_3-C_7)$-cycloakyl,
$R^8$ and $R^9$ are identical or different and each represents hydrogen, $(C_1-C_6)$-alkyl or $(C_3-C_7)$-cycloalkyl, and $R^3$ represents a phenyl or naphthyl ring, where the rings are optionally mono- or polysubstituted by radicals selected from the group consisting of halogen, hydroxyl, carboxyl, cyano, nitro, trifluoromethyl, trifluoromethoxy, $(C_1-C_6)$-alkyl, $(C_1-C_6)$-alkoxy and $(C_1-C_6)$-alkoxycarbonyl, or a pharmaceutically acceptable salt thereof.

2. The compound according to claim 1 where

A, D, E and G each represents the CH group, $L^1$ and $L^2$ are identical or different and independently of one another each represents one or more radicals selected from the group consisting of hydrogen, fluorine, chlorine, cyano, trifluoromethyl and trifluoromethoxy, $R^1$ represents a radical of the formula $-CON-NR^4R^5$
in which
$R^4$ and $R^5$ are identical or different and each represents hydrogen or $(C_1-C_3)$-alkyl, $R^2$ represent a $4R^7$-piperazin-1-yl radical,
which is optionally substituted by one to three hydroxyl groups and/or by a radical of the formula $-NR^8R^9$
in which
$R^7$ represents hydrogen, $(C_1-C_4)$-alkyl, hydroxy-$(C_1-C_4)$-alkyl or $(C_3-C_6)$-cycloalkyl,
and $R^3$ represents phenyl ring, which is optionally mono- or polysubstituted by radicals selected from the group consisting of fluorine, chlorine, cyano, trifluoromethyl and trifluoromethoxy, or a pharmaceutically acceptable salt thereof.

3. A compound according to claim 1 where

A, D and E each represents a CH group,

G represents a CH group, $L^1$ and $L^2$ each represents hydrogen, $R^1$ represents a radical of the formula $-CO-NR^4R^5$,
in which
$R^4$ and $R^5$ each represent hydrogen, $R^2$ represents a 4-$R^7$-piperazin-1-yl radical
in which
$R^7$ represents hydrogen, $(C_1-C_4)$-alkyl or $(C_3-C_6)$-cycloalkyl, and $R^3$ represents a phenyl radical, or a pharmaceutically acceptable salt thereof.

4. (S)-N-{{(1R,2R)-2-{4-{[2-(4-Methyl-piperazin-1-yl)-benzimidazol-1-yl]methyl}-phenyl}cyclohex-1-yl}carbonyl}-phenylglycinamide or a pharmaceutically acceptable salt thereof.

5. A process for preparing compounds of the general formula (I) according to claim 1, characterized in that (A) a compound of the general formula (II)

in which $L^2$ is as defined in claim 1,

T represents $(C_1-C_4)$-alkyl, and

V represents a suitable leaving group, is initially coverted by reaction with a compound of the formula (III)

in which

A, D, E, G and $L^1$ are each as defined in claim 1 and $R^{11}$ has the meaning of $R^2$ given in claim 1, where amino and hydroxyl functions are optionally blocked by suitable amino or hydroxyl protective groups, in inert solvent, depending on the definition of $R^{11}$ optionally in the presence of a base, into a compound of the formula (IV)

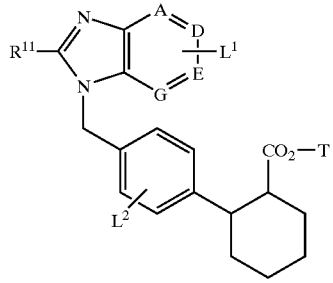

(IV), in which $R^{11}$, A, D, E, G, $L^1$, $L^2$ and T are each as defined above, which is converted in a subsequent step using acid or base into the corresponding carboxylic acid of the general formula (V)

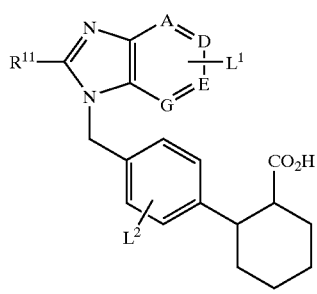

(V), in which $R^{11}$, A, D, E, G, $L^1$ and $L^2$ are each as defined above, which is subsequently reacted with a compound of the general formula

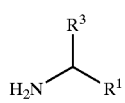

(VI), in which $R^1$ and $R^2$ are each as defined in claim 1 in inert solvent, and, if $R^{11}$ carries one of the abovementioned protective groups, this is optionally removed by customary methods either in the hydrolysis to the acids (IV)→(V) or after the reaction with the compound of the formula (VI), or (B) if $R^2$ of structure (I) shown in claim 1 represents a saturated heterocycle which is attached directly via a nitrogen atom to the imidazole ring, the abovementioned compound of the formula (II) is initially converted with a compound of the formula (IIIa)

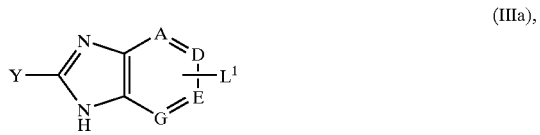

(IIIa), in which

A, D, E, G and $L^1$ are each as defined in claim 1 and

Y represents halogen or mesyl, in inert solvent into the corresponding compound of the formula (VII)

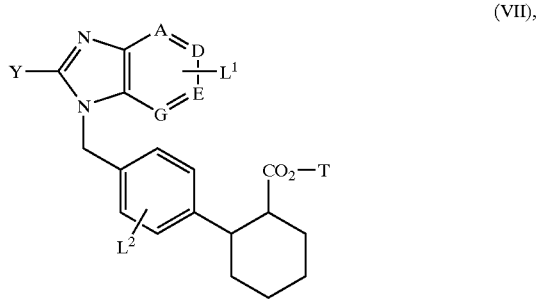

(VII), in which

Y, A, D, E, G, $L^1$, $L^2$ and T are each as defined above, which is reacted in a subsequent step with a compound of the formula (VIII)

$HNR^{12}R^{13}$      (VIII)

in which $R^{12}$ and $R^{13}$ together with the nitrogen atom form a heterocycle according to the definition of $R^2$ to give a compound of the formula (IX)

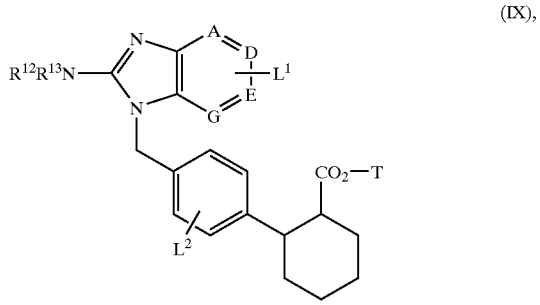

(IX), in which

A, D, E, G, $L^1$, $L^2$, $R^{12}$, $R^{13}$ and T are each as defined above, which is, in the subsequent steps, converted as described under (A) by hydrolysis into the corresponding carboxylic acid of the formula (X)

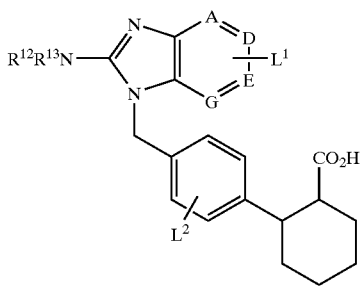

(X), in which

A, D, E, G, $L^1$, $L^2$, $R^{12}$, and $R^{13}$ are each defined above, and this compound is subsequently reacted with the compound of the formula (VI) according to known methods for preparing amides from carboxylic acids and amines and, if appropriate, converted into the corresponding salts by reaction with an acid.

6. A pharmaceutical composition comprising a compound of the general formula (I) according to claim 1 in admixture with at least one pharmaceutically acceptable, essentially non-toxic carrier or excipient.

7. The process of claim 5 wherein T of formula II represents methyl or tert-butyl.

8. The process of claim 5 wherein V of formula II represents halogen, mesylate or tosylate.

9. The process of claim 8 wherein V represents bromine.

10. The process of claim 5 wherein the group Y of structure IIIa represents chorine or bromine.

11. A method of treatment of an ischaemic brain disorder in a mammal, comprising administering an effective amount of a compound of claim 1.

12. The method of claim 11 wherein said mammal is human.

13. The method of claim 11 wherein said ischaemic brain disorder is stroke, reperfusion damage, or brain trauma.

\* \* \* \* \*